United States Patent [19]

Sodomann et al.

[11] 4,006,191
[45] Feb. 1, 1977

[54] PROCESS FOR THE PREPARATION OF ARALKYL MONOHYDROPEROXIDES

[75] Inventors: Heinrich Sodomann; Bruno Hauschulz; Günther Althoff, all of Gladbeck, Germany

[73] Assignee: Phenolchemie GmbH, Gladbeck, Germany

[22] Filed: Jan. 9, 1969

[21] Appl. No.: 791,539

[30] Foreign Application Priority Data

Jan. 13, 1968 Germany ........................ 1668575

[52] U.S. Cl. ............................................. 260/610 B
[51] Int. Cl.$^2$ ........................................ C07C 179/02
[58] Field of Search ................... 260/610 B, 610 A
[56] References Cited

UNITED STATES PATENTS

| 2,249,986 | 7/1941 | Smith ................................ 260/635 |
| 2,515,279 | 7/1950 | Hoeuen ............................. 260/667 |
| 3,388,046 | 6/1968 | Hendrix ............................. 203/18 |

FOREIGN PATENTS OR APPLICATIONS 672,923  10/1963  Canada ..................... 260/610 B
676,772   8/1952  United Kingdom ........... 260/610 B

OTHER PUBLICATIONS

Fisher et al., "Reprint Industrial and Engineering Chem.", vol. 47, pp. 1368–1373.

*Primary Examiner*—James O. Thomas, Jr.
*Assistant Examiner*—W. B. Lone
*Attorney, Agent, or Firm*—Burgess, Dinklage & Sprung

[57] ABSTRACT

Preparation of aralkyl monohydroperoxides comprising oxidizing an alkyl aromatic hydrocarbon in the liquid state by contacting the latter with oxygen or an oxygen containing gas at a temperature of about 40° to 135° C in the absence of any water, acid binding agent or reaction promoting agent, thereafter introducing the oxidate without cooling into a treatment zone maintained under conditions of pressure and vacuum whereby the unreacted hydrocarbon is evaporated, the heat required for the evaporation being solely the heat of formulation of the aralkyl monohydroperoxides.

4 Claims, 1 Drawing Figure

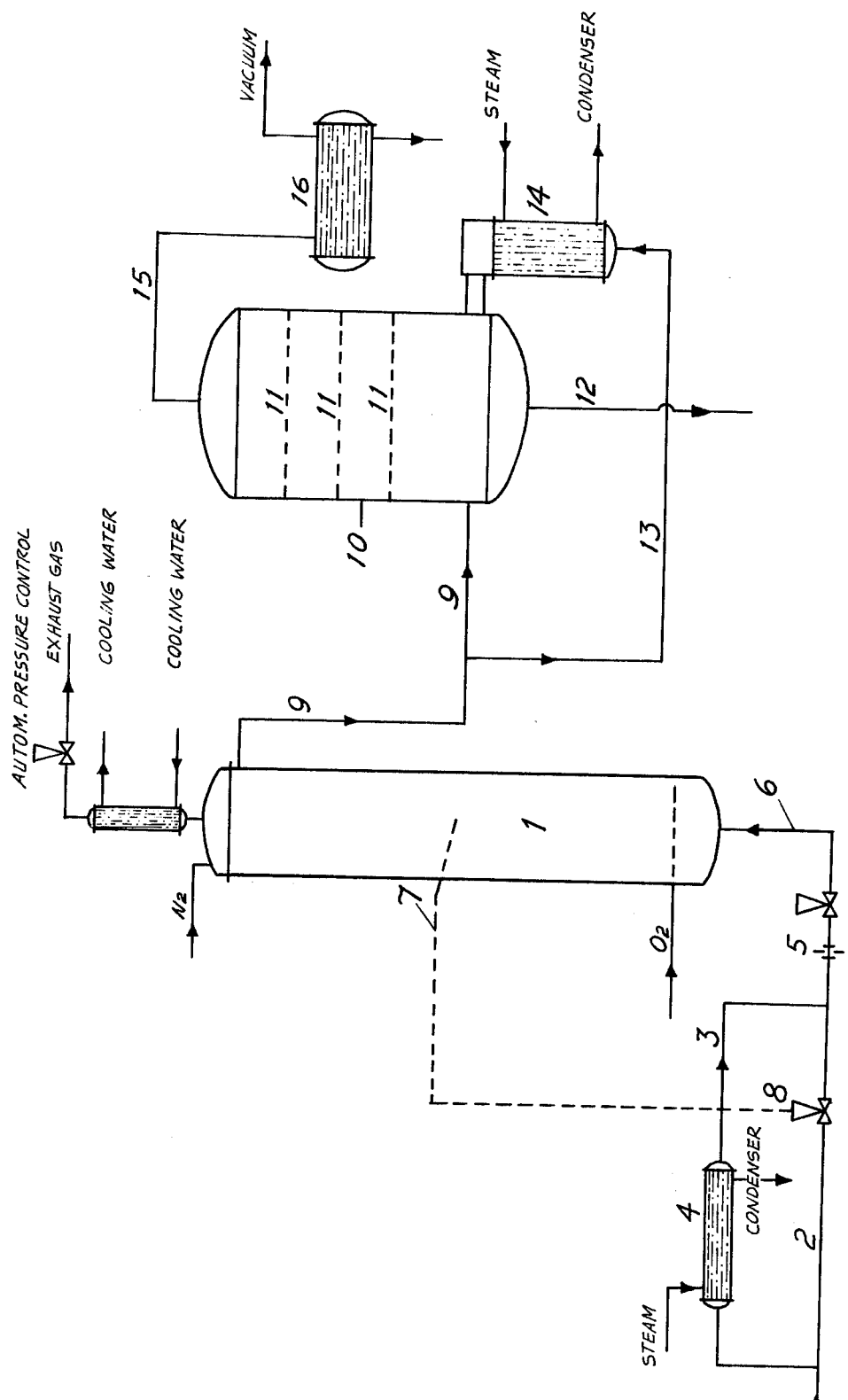

PROCESS FOR THE PREPARATION OF ARALKYL MONOHYDROPEROXIDES

This invention relates to an improved process for the oxidation of alkyl aromatic hydrocarbons to provide aralkyl monohydroperoxides.

The oxidation of alkyl aromatic hydrocarbons and particularly the oxidation of isopropylbenzene to isopropylbenzene hydroperoxide, has achieved considerable technical importance in recent years. This oxidation reaction and the preparation of phenol and acetone from isopropylbenzene hydroperoxide are based on work which was carried out by Hock and Lang(-(BERICHTE DER DEUTSCHEN CHEM. GESELLSCHAFT (1944), Vol. 77, pp. 257 to 264)). In this early process, isopropylbenzene is oxidized with oxygen or gases containing oxygen to the corresponding hydroperoxide. Thereafter the hydroperoxide is split to form phenol and acetone by means of mineral acids such as sulfuric acid. The splitting process is followed by a number of additional process steps, which consist mainly in separating by distillation the substances which are present in the resultant reaction product.

In the preparation of aralkyl monohydroperoxides, the starting hydrocarbon is treated in the liquid state with oxygen or gases containing oxygen, at temperatures ranging, generally between about 40° and 135° C. The latter oxidation procedure has involved the addition of alkalies. Not until recently has it been established that the presence of alkali or other stabilizing agent in the oxidation is not particularly advantageous. The oxidation yields obtained by such procedures carried out in the presence of alkali are generally substantially lower than those which are obtained in the absence of any alkaline reacting substances. According to a later procedure, the oxidation reaction has therefore been conducted in a pH range of from about 3 to 6, without the addition of reaction-promoting substances, and at the same time an oxidation medium has been used which is substantially water-free.

It is known that the oxidation yield depends on a number of factors, among which the temperature and the concentration of cumene hydroperoxide in the oxidation reactor are very important. Other factors influencing the oxidation yield include pressure, detention time, reaction material, etc.

The economic feasibility of the phenol synthesis by the cumene process accordingly depends mainly on achieving the highest possible oxidation yield. This is all the more necessary because, later on in the process, that is during the cleavage and the processing of the cleavage product, considerable losses can and do occur.

In order to eliminate the heat that develops during the oxidation, a process and an apparatus have been described for conducting the oxidation of alkyl aromatic or hydroaromatic hydrocarbons to hydroperoxides, wherein the oxidation of the hydrocarbons present in the liquid state is carried out in a most complex apparatus at about 90° to 135° C by means of oxygen or gases containing oxygen, in the presence of acid-binding substances. This process is characterized in that the oxidation product, after having been subjected to washing in order to remove the acid-binding agent or its conversion products, is caused to flow along the outer walls of the oxidation tube at reduced pressure in order to remove therefrom the heat that has been developed in the oxidation and to partially evaporate the hydrocarbon contained in this oxidation product.

It has been found that carrying out the known process under technical conditions is not only extremely difficult but that it does not produce the expected yields of product. Most of the heat in the oxidate is therefore removed by the washing of the oxidate, this having been found to be necessary in this process. The washing out of the salts from the oxidate is also necessary, in spite of the considerable heat loss which this entails, because without such washing, the reactor chambers through which the oxidate flows are quickly encrusted with the result that transfer of heat is hardly possible. The technical performance of this process has therefore been impossible, if only for these reasons.

In the search for an economical method of improving the oxidation yields of aralkyl monohydroperoxides, in which all of the heat that develops in the oxidation is utilized or recycled into the process the applicants have discovered a technically very simple process which provides for the highest possible oxidation yields along with optimum utilization of the heat that is developed in the oxidation. The process of the invention comprises oxidizing a hydrocarbon having the formula:

wherein Ar designates an aromatic hydrocarbon radical and R an aliphatic hydrocarbon radical in the presence of oxygen or a gas containing oxygen, at a temperature of between 40° and 135° C in the substantially complete absence of any alkali and water, at a pH of 3 to 6, the resultant oxidation product being fed directly without further treatment directly into a treatment zone in which conditions of pressure and vacuum are maintained so that, without the additional input of heat, the unreacted hydrocarbons are evaporated, substantially all of the heat present in the oxidation product, i.e., based on the heat of formation of the produced aralkyl monohydroperoxides being used for the evaporation of unreacted hydrocarbon.

The oxidation is carried out in oxidation towers which contain no packing of any kind. The oxygen and cumene are fed into the bottom of this reactor, and the oxygen, or gas containing oxygen, is caused to flow through diffusing means to provide a fine distribution of the gas in the liquid hydrocarbon. The oxidation is conducted only to such an extent that less than 30% of the starting hydrocarbon is converted into cumene hydroperoxide. On the other hand, for economical reasons it has been found not to be advantageous to react less than 5% of the hydrocarbon, even though under these circumstances the oxidation yield is particularly high, and might exceed 95%. This very good yield, however, is offset by the fact that more than 90% of the starting hydrocarbon has to be removed by distillation, which decreases the efficiency and therewith economic advantages of the process.

It has been found that the most economical procedure is to convert 10 to 20% of the starting hydrocarbon to cumene hydroperoxide. In this range the oxidation yield amounts to about 90 to 94%, the 94% yield corresponding to an oxidate of about 10% cumene hydroperoxide and the 90% yield to an oxidate of about 20% cumene hydroperoxide. From this it can be seen that a 10% difference in the cumene hydroperoxide content in the oxidate results in a difference of about 4% in the yield. This means on the average, assuming that the oxidation conditions are the same, that, in the conversion percentage range above noted a drop of about 0.4% in the yield is produced for each percentage point of increase in the cumene hydroperoxide content. These data are based on oxidation temperatures ranging from about 125° to 130° C, and they change to some extent above and below these reaction temperatures.

The present process is intended to bring about the result that all of the heat present in the oxidate, and which corresponds to the heat of formation of the cumene hydroperoxide, is rendered usable by direct heat exchange, this being accomplished under conditions whereby the concentration of cumene hydroperoxide in the oxidate is increased without losses in yield. As has already been noted, the oxidation yield is to a great extent dependent on the cumene hydroperoxide content in the oxidate. For example, the yield of an oxidate having a content of about 10% cumene hydroperoxide amounts to 93.2%. The oxidation in this instance was carried out at a temperature of 130° C in the absence of any reaction promoting additives. Under these conditions of operation, a pH value of 3.4 established itself in the oxidation medium. The resultant oxidate was thereafter fed directly, without the interposition of a washing process, into a vacuum apparatus. At a vacuum of about 100 Torr, the amount of cumene that was evaporated was such that the residual product contained about 17% cumene hydroperoxide. In the concentrated residual oxidate which was thusly obtained the yield of hydroperoxide was determined to be 93.2%, i.e., the process as just described was carried out without any loss of yield.

In contrast, the oxidation yield is considerably lower when the oxidation is carried out directly in the reactor to a 17% cumene hydroperoxide content. The yield determined in an oxidate produced in this manner amounts to only 90.4%.

The considerable technical advance achieved by the process in accordance with the invention lies in the fact that it is possible to achieve an increase in yield by carrying out the oxidation in a two-step system. In the first step, the cumene hydroperoxide content in the oxidate is kept as low as possible so as to achieve a high oxidation yield, but in the second step which directly follows the first and in which no additional heat is introduced an enrichment of the cumene hydroperoxide content is accomplished.

In the process of the invention, there is an entirely special advantage in the fact that, the heat of formation of the cumene hydroperoxide is utilized for the carrying out of the second step of the process. Previously the cumene entering the oxidation reactor has been heated to a temperature corresponding approximately to the reaction temperature in the reactor. This was considered necessary in order to achieve a uniform oxidation.

In the meantime, however, it has been found and confirmed that the oxidation can also be satisfactorily carried out if the cumene is introduced into the oxidation reactor at a temperature that is substantially lower than the reaction temperature. Studies have shown that uniform oxidation is possible even when the cumene entering the reactor is at a temperature which corresponds approximately to the ambient temperature.

According to the procedure as herein disclosed, the only important factor is how high the degree of oxidation is, and therefore how much heat is released based on the heat of formation. The process can be described by noting that, at a higher concentration of cumene hydroperoxide in the reactor, the oxidation heat which is formed per unit of volume is greater than it is for lower cumene hydroperoxide contents. The temperature of the cumene which is fed into the reactor can be so low that the entire heat of formation which is developed in the formation of the cumene hydroperoxide from cumene, is transferred to the cumene which is fed into the reactor. With a cumene hydroperoxide content in the oxidate of about 15%, and at a reaction temperature of 130° C, the temperature of the entering cumene can amount to about 50° C. The heating of the cumene from 50° to 130° C is carried out in the reactor and utilizes the heat of formation that is developed in the oxidation of the cumene to cumene hydroperoxide.

In order to make it possible to utilize the heat of formation which is liberated in the oxidation regardless of the conditions of the oxidation, the entire required amount of cumene to be introduced is divided up between two feed lines. The one line carries "cold" cumene, while the other carries "hot" cumene into the reactor. To maintain the desired reaction temperature in the reactor, the rate of flow of the "cold cumene" is controlled through a relay which in turn is operated by a thermostat in the reactor, so that, when the reaction temperature in the reactor is increased, more "cold cumene" is automatically delivered to the reactor, and when the reaction temperature falls below the desired level, less "cold cumene" is atomically delivered to the reactor. The "hot cumene" can be prepared in the necessary quantity by means of a heater or heat exchanger. The "cold cumene" and the "hot cumene" are combined just prior to entry into the reactor. The use of this procedure in technical operation has established that it has no adverse effect of any kind on the results of the oxidation, and that, contrary to expectations and the procedures known hitherto, the procedure is substantially improved, in that it is possible to carry out the oxidation in a substantially trouble-free and extremely uniform manner.

As already mentioned, special significance is to be attached to the fact that all of the heat of formation in the reaction medium is saved, and that this heat of reaction is used in a second step for the purpose of increasing the cumene hydroperoxide content in the oxidate.

The process in accordance with the invention will be further described in conjunction with the schematic drawing forming part of the disclosure.

Before the cumene enters into the reaction vessel 1, it is divided up so that it flows in two lines 2 and 3, line 2 carrying "cold cumene" while the necessary amount of "hot cumene" flows through line 3, the cumene having been heated up by heat exchanger 4. At a point in advance of the flow meter 5, the "cold cumene" and the "hot cumene" are combined and delivered at a corresponding mean temperature into the bottom of the reaction vessel 1. At a point which preceeds the entry of the combined cumene into the reactor a thermometer 6 is installed, by means of which the input temperature of the cumene can always be determined. Inside of the reaction vessel, at any desired point but generally in the approximate center, there is a thermostat by which the temperature desired in the reaction vessel can be set and automatically maintained. The temperature is maintained by increasing or decreasing the rate of flow as required by means of the control valve 8 that is installed in the "cold cumene" line. In this manner, all of the heat that is developed in the oxidation of the cumene to cumene hydroperoxide is used for the purpose of heating the input cumene and therewith the entire reaction mixture to the desired reaction temperature. At the upper end the hot oxidate continuously emerges through line 9 and is delivered by the pressure of the reactor into a vessel 10 maintained under vacuum without the interposition of any washing towers or pumps. The vacuum vessel can contain separating trays 11, which can be of any desired construction. The number of these trays 11 can be greater than one, the only limitation being that, where there are many such trays, a vacuum of less than 150 Torr is required to be maintained in the lower part of this vacuum apparatus because of the pressure losses that occur. When other types of packing are used, a corresponding vacuum should be present in the lower part of the apparatus. The reaction product is discharged from the vacuum apparatus at the bottom thereof through line 12.

If an additional concentrating action is desired, the oxidate can be passed through line 13 and a heat exchanger 14. The evaporated cumene is carried through line 15 into the condenser 16 and is there condensed.

The following Examples are given in order to more clearly illustrate the invention, but are not to be construed as limiting. The Examples clearly show the technical advance achieved by the instant process as well as the economic advantages achieved therewith.

EXAMPLE 1a

Process of the Invention

Cumene and oxygen were introduced cocurrently into the bottom of an oxidation reactor having a height of 15 m and a diameter of 1.5 m. The pressure at the head of the reactor was adjusted to 4 atmospheres gauge. The oxidation was carried out in a substantially water-free medium without the addition of any acid-binding agent. Furthermore, no additives were used which might serve to promote the reaction. The oxidation was conducted to the extent that the cumene hydroperoxide content in the oxidate amounted to 12%. Cumene and oxygen were continuously added to the bottom of the reactor, while the oxidate was continuously withdrawn from the top of the reactor. In the oxidate the yield of hydroperoxide was determined to be 92.5%.

The 12% oxidate was then fed directly into an apparatus in which a vacuum of 30 to 40 Torr was maintained. Under these conditions, a temperature of about 60° C was established. At this temperature a reaction product was formed in the bottom of the apparatus which had a cumene hydroperoxide content of 20.5%.

This value represents an increase in concentration of slightly better than 70% as compared with the starting product. The yield of hydroperoxide found in this product amounted to 92.5%.

EXAMPLE 1b

Process of the Prior Art

Using the same oxidation reactor as described in Experiment 1a, the oxidation of cumene was carried out under the same conditions excepting that, in the final stage, the cumene hydroperoxide content amounted to 20.5%. The operaton in this instance was also carried out continuously, i.e., cumene and oxygen were introduced co-currently into the bottom of the reactor while the oxidate was discharged from the top. A yield of 89.5% was established. In comparison with the procedure of the process of the invention, this corresponded to a yield amounting to 3% less in this instance. In other words, the process of the invention made it possible to achieve an increase in yield of 3% for the same cumene hydroperoxide concentration, without any additional expenditure of energy.

EXAMPLE 2a

Process of the Invention

Under the same conditions as described under Experiment 1a, an 18% oxidate was prepared. The oxidation yield was determined to amount to 90.4%. In the second step, at a vacuum of 30 to 40 Torr, a reaction product was produced which had a cumene hydroperoxide content of 30.8%. This represents an increase in concentration of better than 70% in comparison with the starting product. The yield of the hydroperoxide product amounted to 90.4%.

EXAMPLE 2b

Process of the Prior Art

Under the same conditions as described under 2a, an oxidate was prepared using the same reactor which had a cumene hydroperoxide content of 30.8%. The yield of hydroperoxide in this product amounted to 85.9%.

Accordingly, a substantially improved yield was achieved by the process according to the invention, i.e., the yield was 4.5% higher. As starting materials for the process not only cumene, but also for instance Diisopropylbenzene, Isopropylnaphthalene, Diisopropylnaphthalene are usable.

We claim:

1. Process for the preparation of aralkyl monohydroperoxides of the formula:

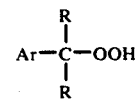

wherein Ar represents phenyl and R represents methyl, which comprises oxidizing a hydrocarbon of the formula:

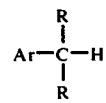

wherein Ar and R are as above defined with a member selected from the group consisting of oxygen and oxygen-containing gases at a temperature of about 40° to 135° C in the absence water, acid binding agents and reaction-promoting additives, to provide a conversion of between 5 to 30% hydroperoxide, directly thereafter in a second step directly introducing the oxidation product thereby obtained into a treatment zone maintained at a pressure of less than 150 Torr and under conditions whereby without any further heat input, unreacted hydrocarbons present in the oxidation product are evaporated and separated from said hydroperoxide, the heat required for the evaporation being derived solely from the heat liberated in the formation of the aralkyl monohydroperoxides.

2. Process according to claim 1 wherein the oxidation is conducted to provide a conversion of between 10 to 20% hydroperoxide.

3. Process according to claim 1 wherein the oxidation is carried out at a pH of 3–6.

4. Process according to claim 1 wherein said second step is conducted under a vacuum of 30 to 40 Torr.

* * * * *